(12) United States Patent
Nichols et al.

(10) Patent No.: US 8,025,679 B2
(45) Date of Patent: Sep. 27, 2011

(54) METHOD FOR SPINAL STABILIZATION USING A ROD CONNECTOR

(75) Inventors: David Nichols, Trumbell, CT (US); Eric Finley, San Diego, CA (US)

(73) Assignee: Howmedica Osteonics Corp., Mahwah, NJ (US)

( * ) Notice: Subject to any disclaimer, the term of this patent is extended or adjusted under 35 U.S.C. 154(b) by 1127 days.

(21) Appl. No.: 11/062,510

(22) Filed: Feb. 22, 2005

(65) Prior Publication Data

US 2005/0192569 A1   Sep. 1, 2005

Related U.S. Application Data

(63) Continuation of application No. 10/012,127, filed on Dec. 7, 2001, now Pat. No. 6,875,211, which is a continuation of application No. 09/535,776, filed on Mar. 28, 2000, now abandoned.

(60) Provisional application No. 60/126,997, filed on Mar. 30, 1999.

(51) Int. Cl.
*A61B 17/70* (2006.01)
(52) U.S. Cl. .................................................. 606/252
(58) Field of Classification Search .......... 606/250–253, 606/60, 246, 260, 270, 278–279
See application file for complete search history.

(56) References Cited

U.S. PATENT DOCUMENTS

| | | | |
|---|---|---|---|
| 768,452 A * | 8/1904 | Hennessy | 403/105 |
| 4,085,744 A | 4/1978 | Lewis et al. | |
| 4,257,409 A | 3/1981 | Bacal et al. | |
| 4,361,141 A | 11/1982 | Tanner | |
| 4,404,967 A | 9/1983 | Bacal et al. | |
| 4,567,884 A | 2/1986 | Edwards | |
| 4,716,894 A | 1/1988 | Lazzeri et al. | |
| 4,773,402 A | 9/1988 | Asher et al. | |
| 5,010,879 A * | 4/1991 | Moriya et al. | 606/276 |
| 5,084,049 A | 1/1992 | Asher et al. | |
| 5,102,412 A | 4/1992 | Rogozinski | |
| 5,112,332 A | 5/1992 | Cozad | |
| 5,116,334 A | 5/1992 | Cozad | |
| 5,127,912 A * | 7/1992 | Ray et al. | 606/250 |
| 5,147,359 A | 9/1992 | Cozad et al. | |

(Continued)

FOREIGN PATENT DOCUMENTS

DE          3807335           9/1989
(Continued)

OTHER PUBLICATIONS

PCT International Search Report for PCT/US 00/08318.

*Primary Examiner* — Thomas C. Barrett
*Assistant Examiner* — Sameh Boles
(74) *Attorney, Agent, or Firm* — Lerner, David, Littenberg, Krumholz & Mentlik, LLP

(57) ABSTRACT

An apparatus is disclosed for connecting first and second elongated spaced apart spinal rods to one another which includes an elongated body portion, a clamp portion depending from the body portion for engaging a spinal rod, the clamp portion defining a deformable clamp body having opposed clamp arms configured for movement between a first position wherein a spinal rod is received between the opposed clamp arms of the clamp body and a second position wherein the spinal rod is securely engaged by the opposed clamp &ms &the clamp body, and structure operatively associated with the clamp body which h configured to effectuate movement of the opposed clamp arms of the clamp body between the first and second positions.

21 Claims, 9 Drawing Sheets

U.S. PATENT DOCUMENTS

| | | |
|---|---|---|
| 5,147,360 A | 9/1992 | Dubousset |
| 5,154,718 A | 10/1992 | Cozad et al. |
| 5,181,917 A | 1/1993 | Rogozinski |
| 5,201,734 A | 4/1993 | Cozad et al. |
| 5,261,907 A | 11/1993 | Vignaud et al. |
| 5,275,600 A | 1/1994 | Allard et al. |
| 5,312,405 A * | 5/1994 | Korotko et al. ............... 606/278 |
| 5,334,203 A | 8/1994 | Wagner |
| 5,352,226 A | 10/1994 | Lin |
| 5,368,594 A | 11/1994 | Martin et al. |
| 5,374,267 A | 12/1994 | Siegal |
| 5,413,602 A | 5/1995 | Metz-Stavenhagen |
| 5,423,818 A * | 6/1995 | Van Hoeck et al. ........... 606/278 |
| 5,439,463 A | 8/1995 | Lin |
| 5,446,465 A | 8/1995 | Diefes et al. |
| 5,454,812 A | 10/1995 | Lin |
| 5,487,742 A | 1/1996 | Cotrel |
| 5,498,263 A | 3/1996 | DiNello et al. |
| 5,522,816 A | 6/1996 | Dinello et al. |
| 5,540,689 A | 7/1996 | Sanders et al. |
| 5,549,612 A * | 8/1996 | Yapp et al. .................... 606/293 |
| 5,575,791 A | 11/1996 | Lin |
| 5,601,552 A | 2/1997 | Cotrel |
| 5,620,444 A | 4/1997 | Assaker |
| 5,624,442 A | 4/1997 | Mellinger et al. |
| 5,630,816 A * | 5/1997 | Kambin ........................ 606/252 |
| 5,651,789 A | 7/1997 | Cotrel |
| 5,667,506 A | 9/1997 | Sutterlin |
| 5,667,507 A | 9/1997 | Corin et al. |
| 5,688,272 A | 11/1997 | Montague et al. |
| 5,702,393 A | 12/1997 | Pfaifer |
| 5,707,372 A | 1/1998 | Errico et al. |
| 5,709,684 A | 1/1998 | Errico et al. |
| 5,709,685 A * | 1/1998 | Dombrowski et al. ....... 606/278 |
| 5,713,900 A | 2/1998 | Benzel et al. |
| 5,716,355 A | 2/1998 | Jackson et al. |
| 5,743,911 A | 4/1998 | Cotrel |
| 5,752,955 A * | 5/1998 | Errico ........................... 606/252 |
| 5,800,548 A * | 9/1998 | Martin et al. ................. 606/253 |
| 5,827,283 A | 10/1998 | Groiso et al. |
| 5,899,903 A | 5/1999 | Cotrel |
| 5,947,966 A | 9/1999 | Drewry et al. |
| 5,964,769 A * | 10/1999 | Wagner et al. ................. 606/74 |
| 5,980,523 A | 11/1999 | Jackson |
| 5,989,251 A * | 11/1999 | Nichols ......................... 606/250 |
| 6,077,263 A | 6/2000 | Ameil et al. |
| 6,083,226 A | 7/2000 | Fiz |
| 6,096,039 A | 8/2000 | Stollenberg et al. |
| 6,113,600 A | 9/2000 | Drummond et al. |
| 6,171,311 B1 * | 1/2001 | Richelsoph ................... 606/252 |
| 6,217,578 B1 | 4/2001 | Crozel et al. |
| 6,306,137 B2 * | 10/2001 | Troxell ......................... 606/252 |
| 6,368,320 B1 * | 4/2002 | Le Couedic et al. .......... 606/250 |
| 6,887,241 B1 * | 5/2005 | McBride et al. ............. 606/86 A |
| 7,066,938 B2 * | 6/2006 | Slivka et al. .................. 606/914 |

FOREIGN PATENT DOCUMENTS

| | | |
|---|---|---|
| EP | 0328883 | 1/1989 |
| EP | 0461374 | 4/1991 |
| EP | 0 578 320 A1 | 1/1994 |
| EP | 0 836 836 | 1/1994 |
| EP | 0 446 092 B1 | 7/1995 |
| EP | 0 813 845 | 12/1997 |
| FR | 2645427 | 10/1990 |
| FR | 2659223 | 9/1991 |
| FR | 2701833 | 2/1993 |
| JP | 2 215455 | 2/1993 |

\* cited by examiner

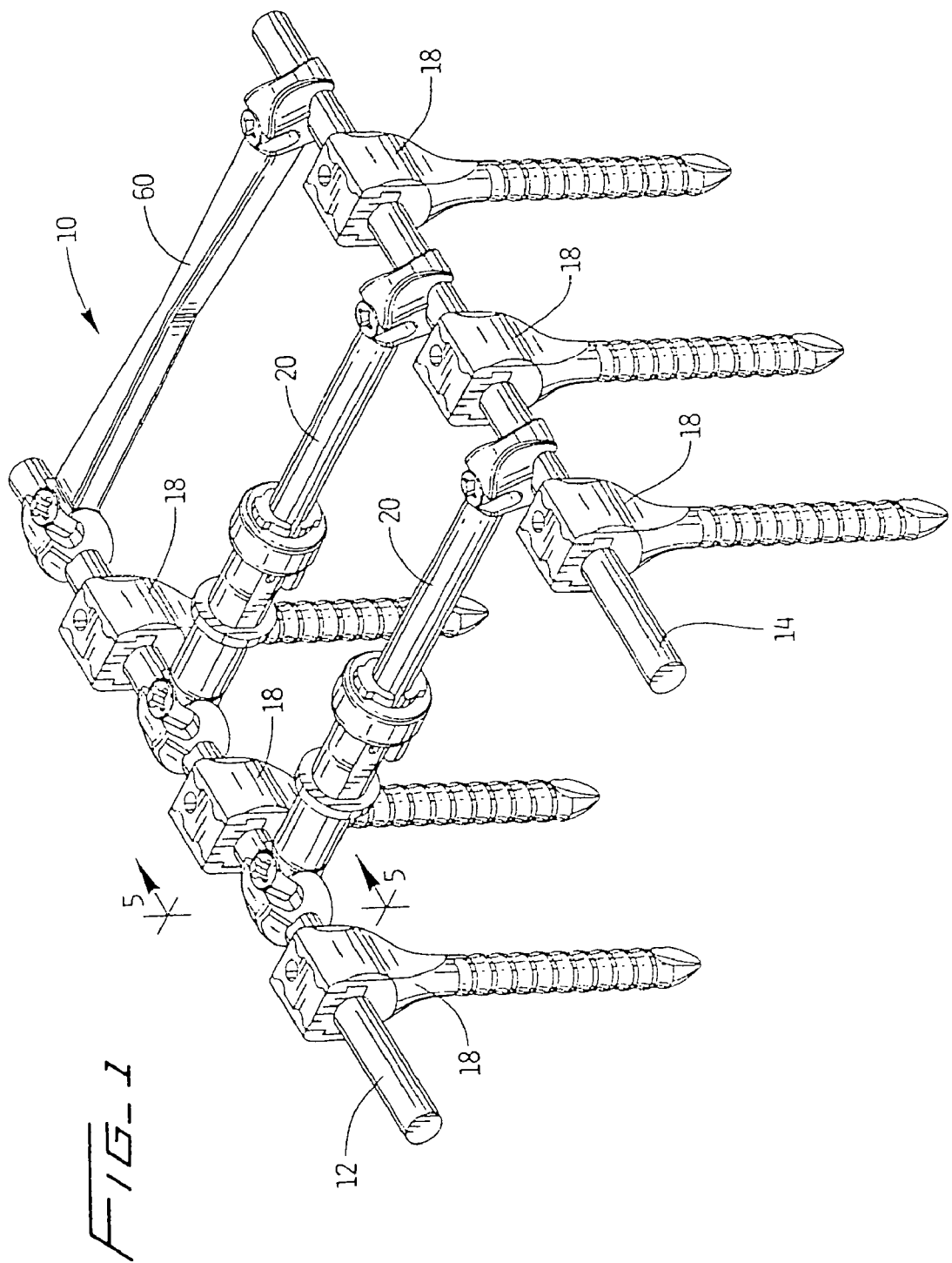

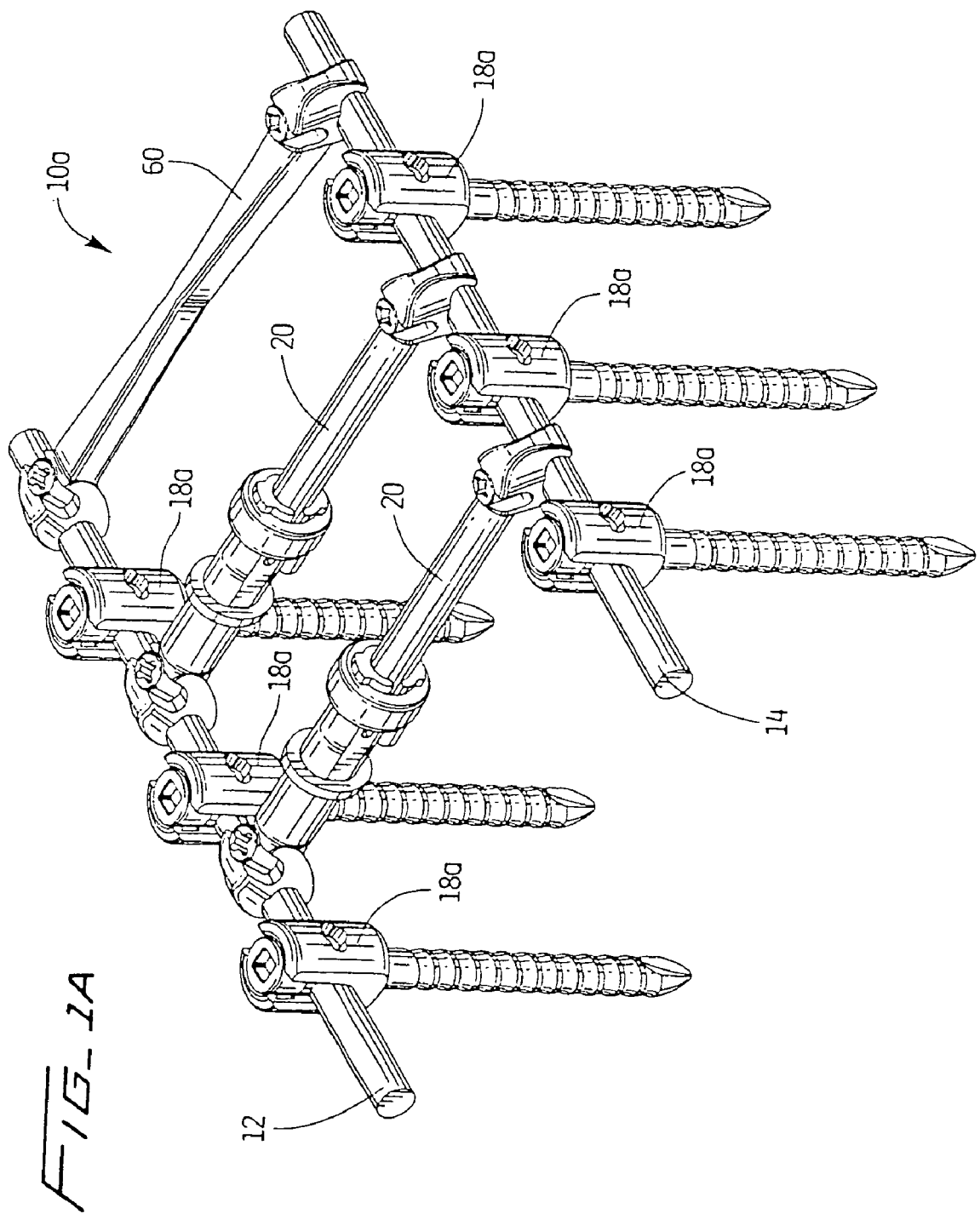

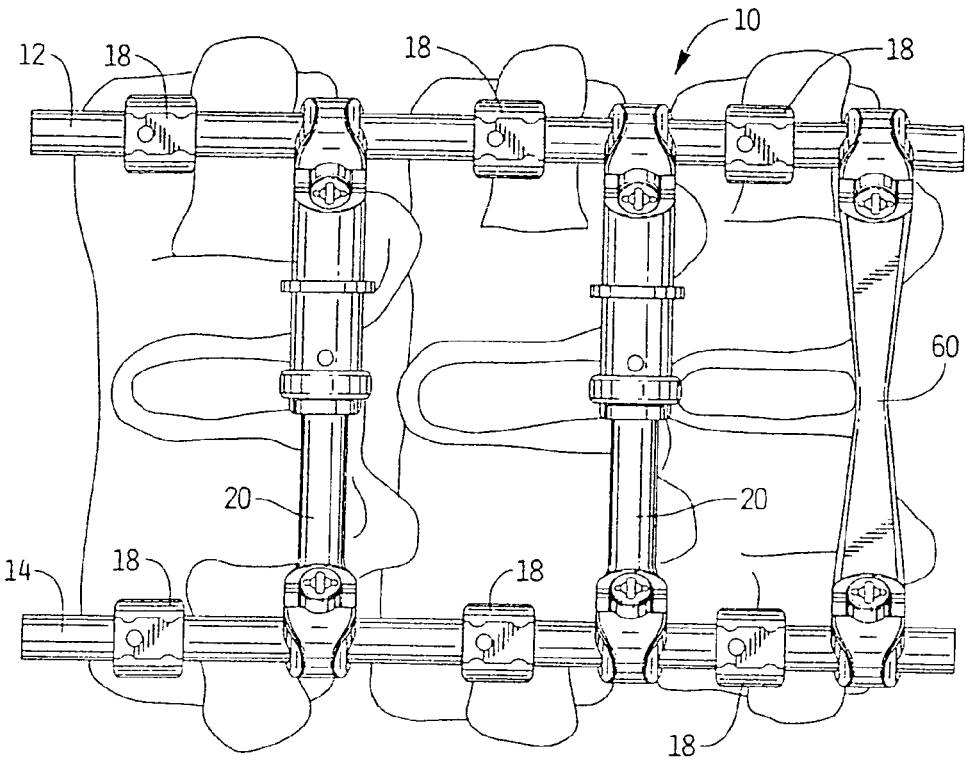
FIG_2
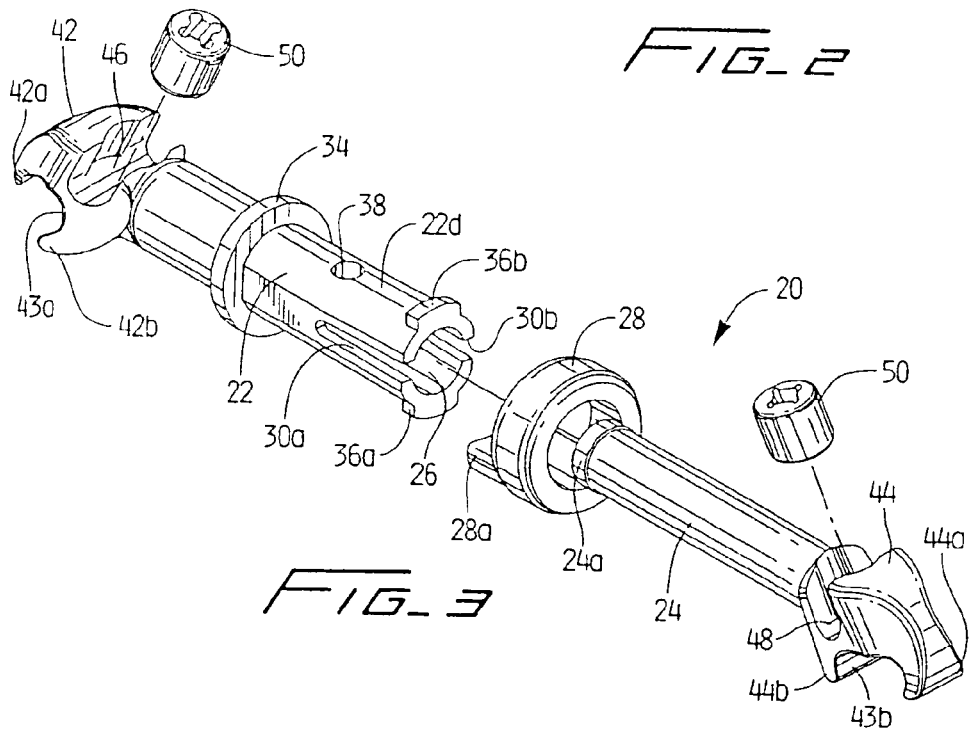
FIG_3

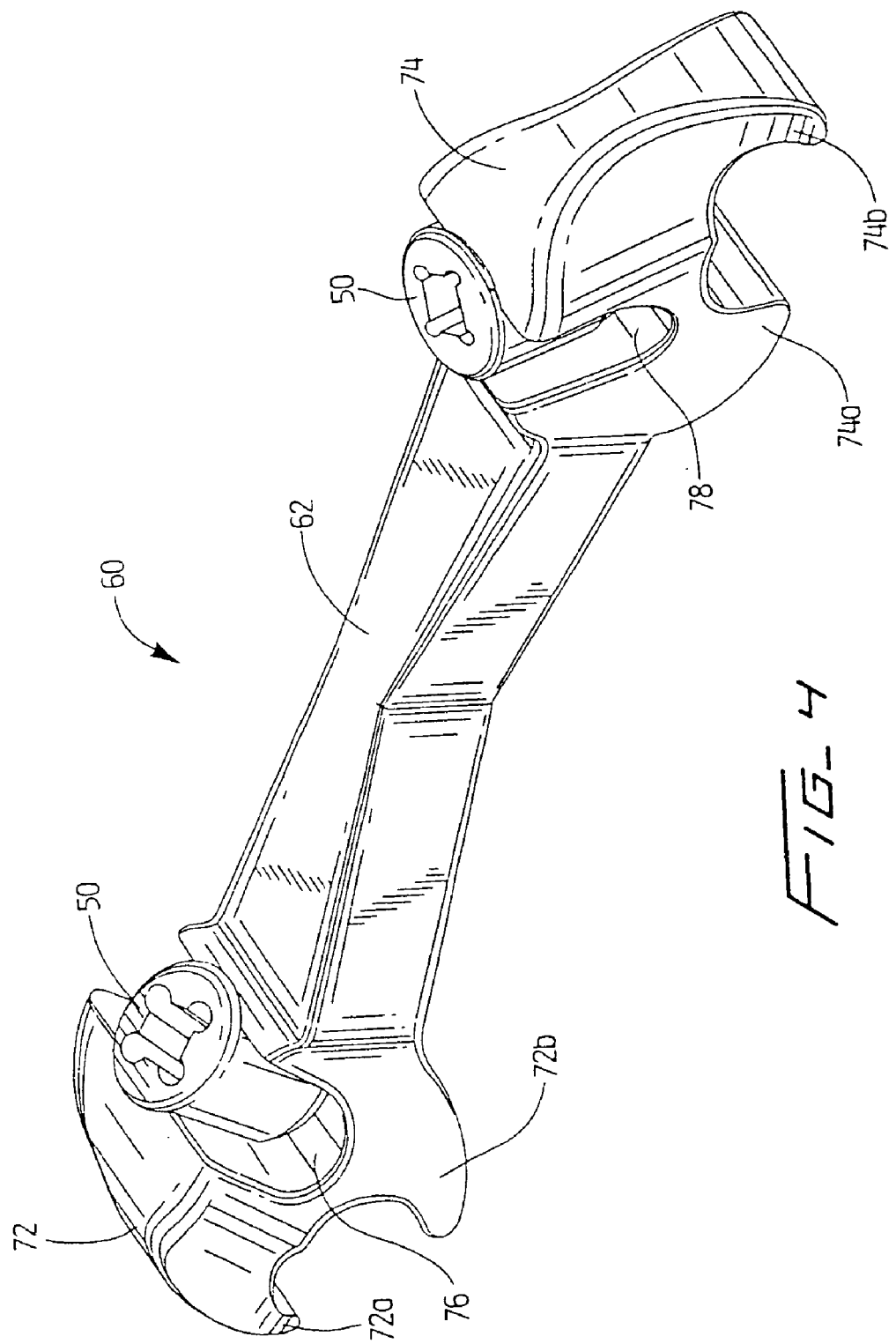

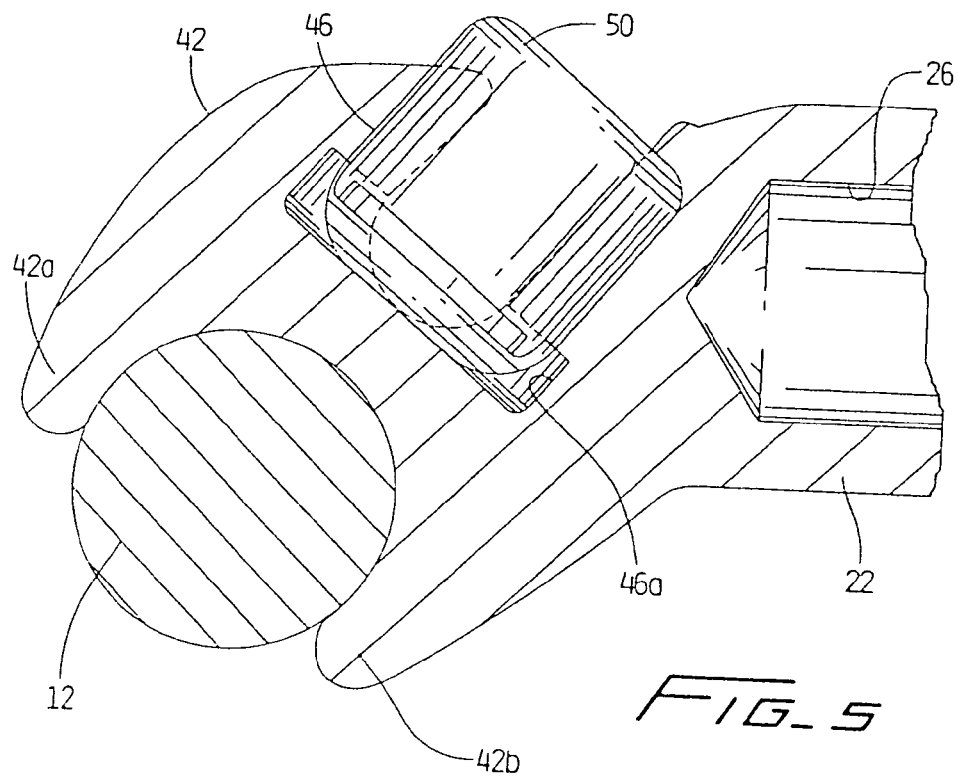
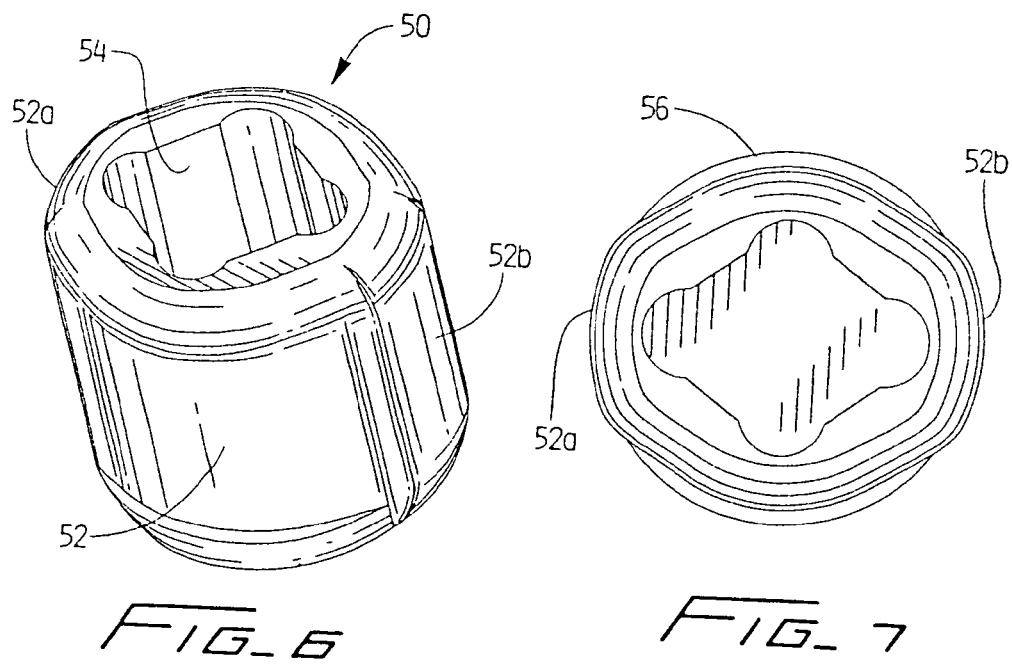

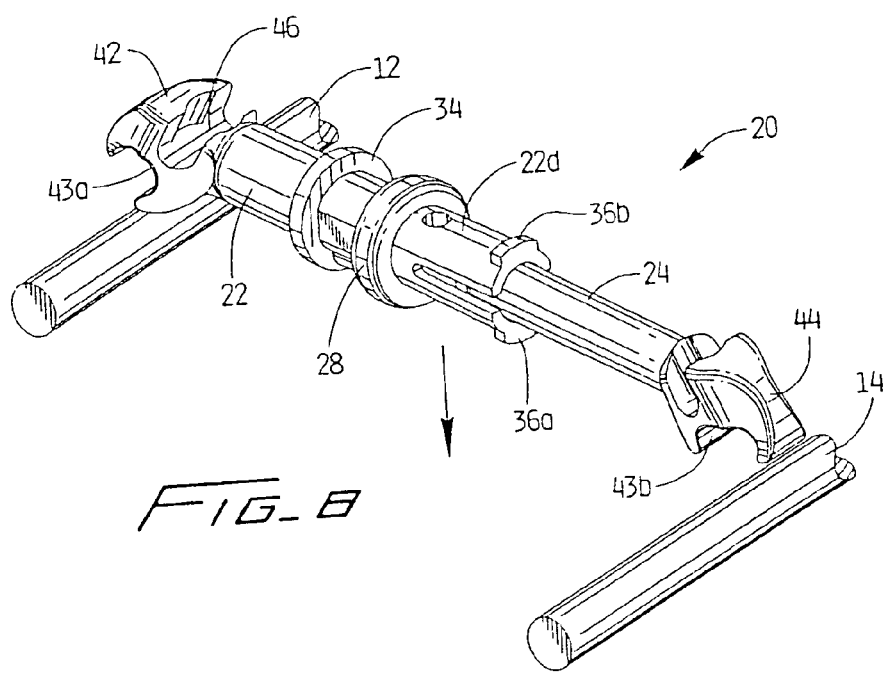
FIG_8
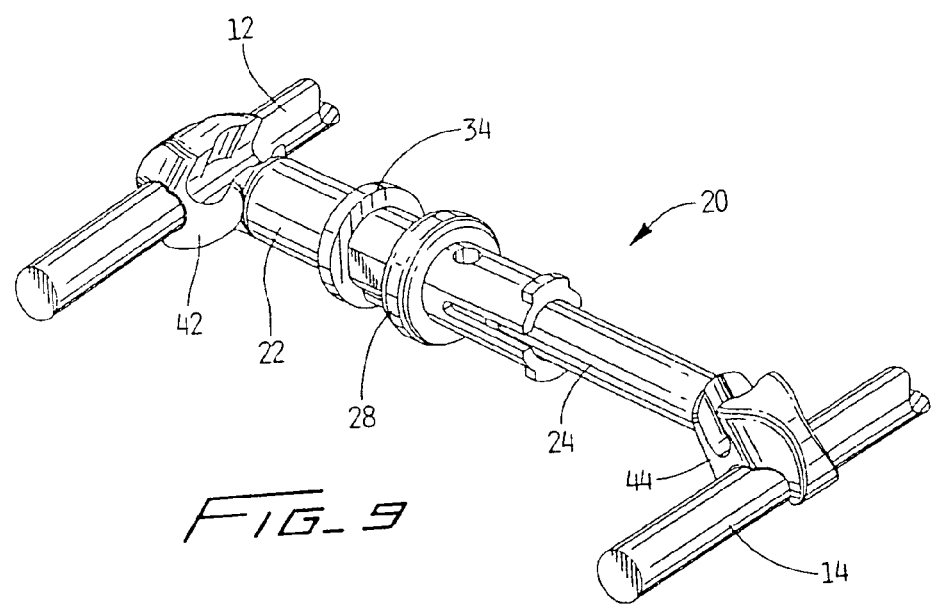
FIG_9

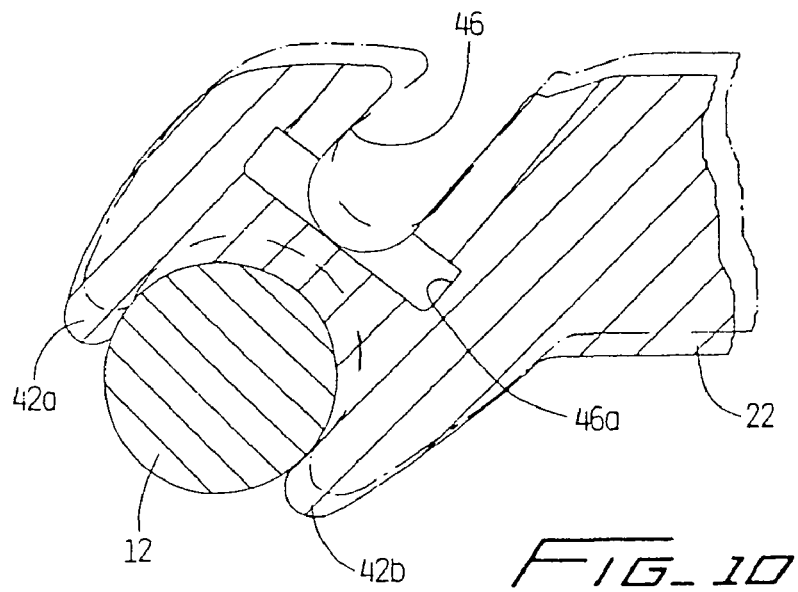
FIG_10
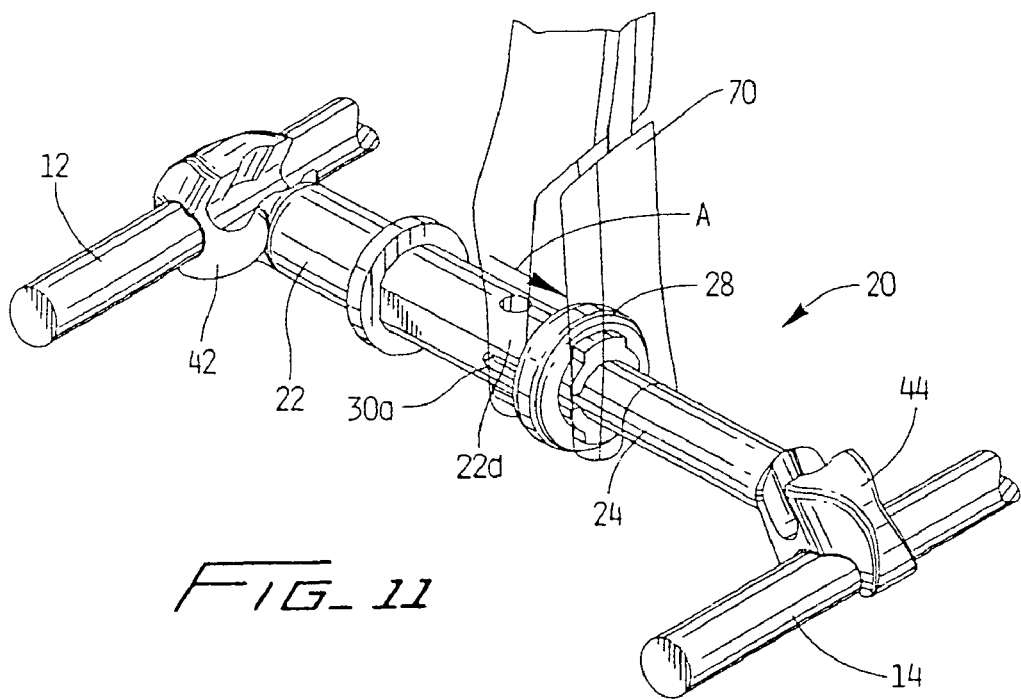
FIG_11

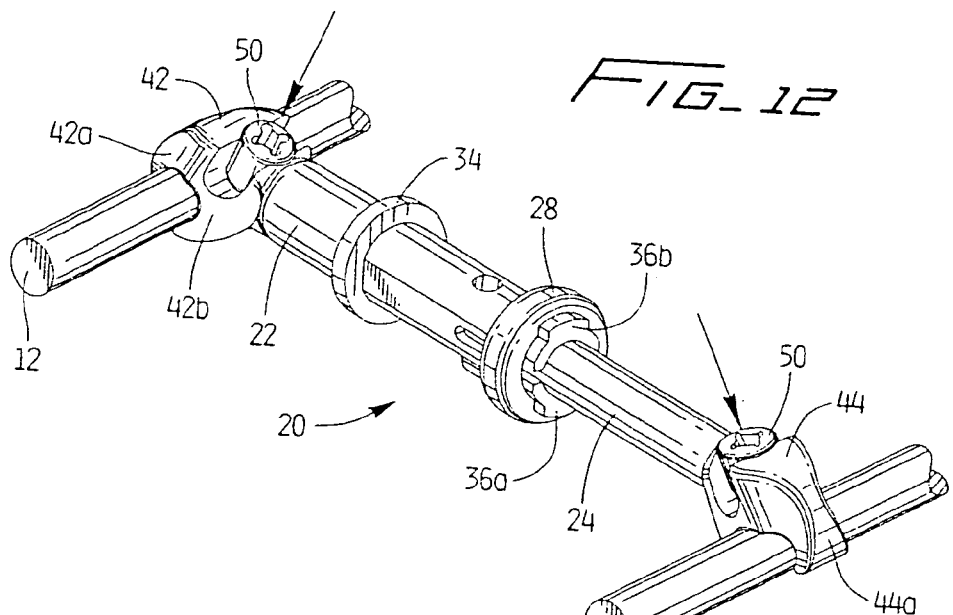
FIG_12
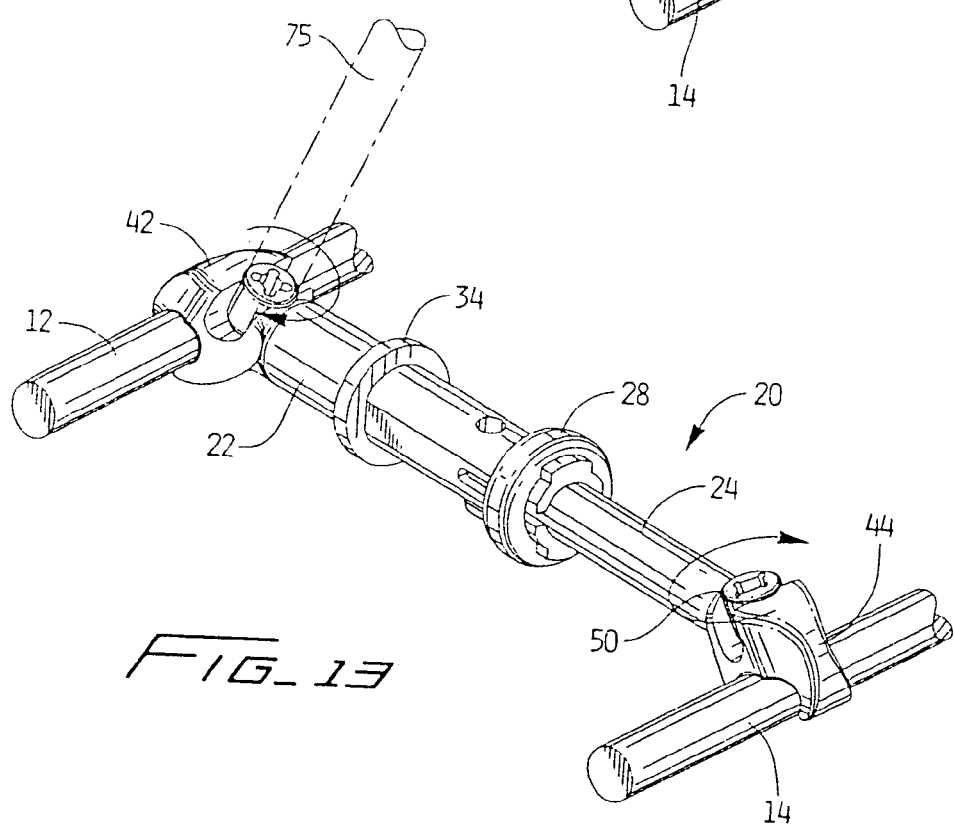
FIG_13

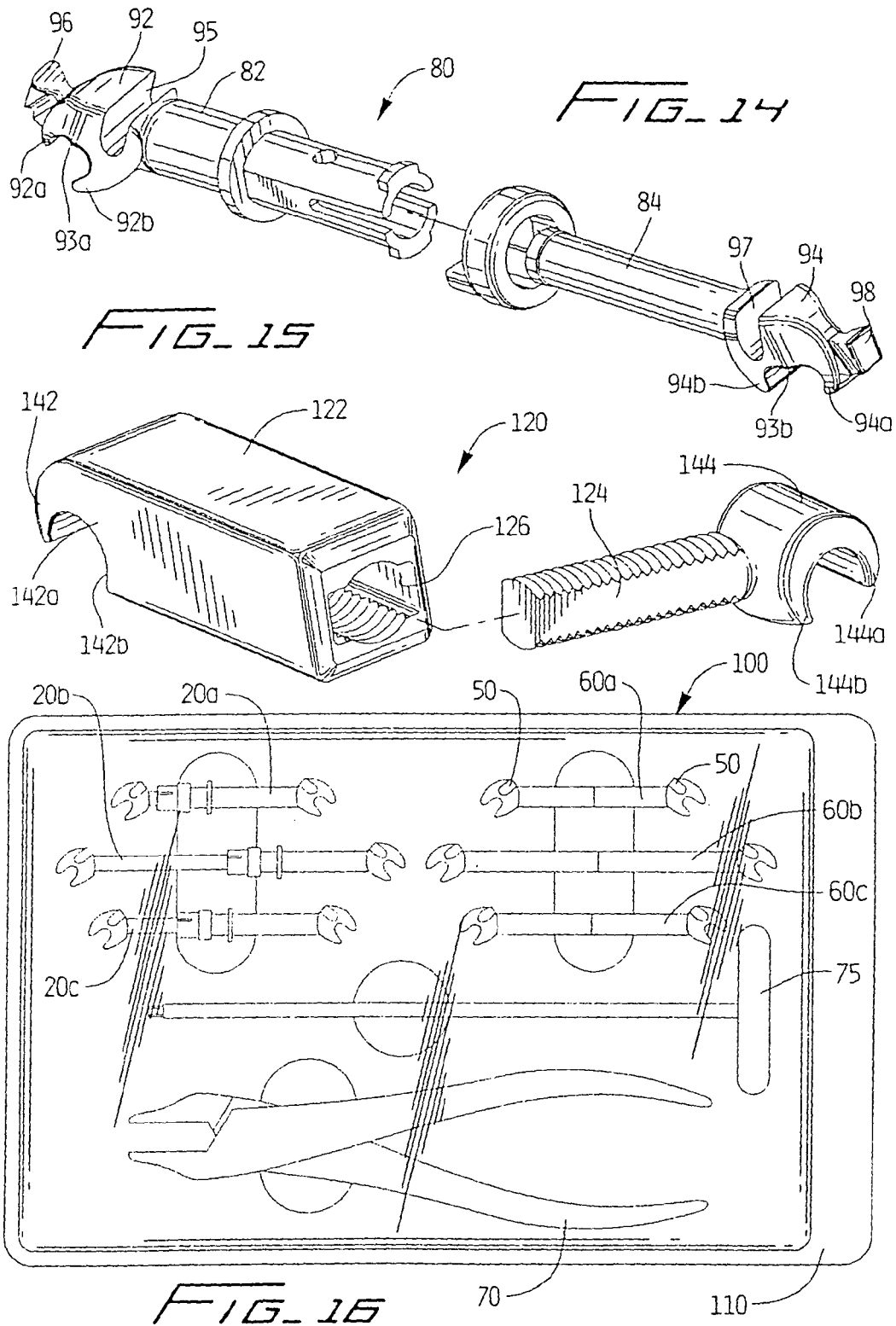

METHOD FOR SPINAL STABILIZATION USING A ROD CONNECTOR

CROSS-REFERENCE TO RELATED APPLICATIONS

This application is a continuation of application Ser. No. 10/012,127, filed on Dec. 7, 2001, which is a continuation of Ser. No. 09/535,776, filed Mar. 28, 2000, now abandoned, which claims the benefit of the filing date of provisional application Ser. No. 60/126,997, filed Mar. 30, 1999, the disclosure of which herein is incorporated by reference in its entirety.

BACKGROUND OF THE DISCLOSURE

1. Field of the Disclosure

The subject disclosure relates to implantable spinal stabilization systems for surgical treatment of spinal disorders, and more particularly, to an apparatus for connecting cylindrical spinal rods of a spinal stabilization system to one another across the spinous process.

2. Background of the Related Art

The spinal column is a complex system of bones and connective tissue which protects critical elements of the nervous system. Despite these complexities, the spine is a highly flexible structure, capable of a high degree of curvature and twist through a wide range of motion. Trauma or developmental irregularities can result is spinal pathologies which limit this range of motion.

For many years, orthopedic surgeons have attempted to correct spinal irregularities and restore stability to traumatized areas of the spine through immobilization. Over the past ten years, spinal implant systems have been developed to achieve immobilization. Examples of such systems are disclosed in U.S. Pat. Nos. 5,102,412 and 5,181,917. Such systems often include spinal instrumentation having connective structures such as elongated rods which are placed on opposite sides of the portion of the spinal column intended to be immobilized. Screws and hooks are commonly utilized to facilitate segmental attachment of such connective structures to the posterior surfaces of the spinal laminae, through the pedicles, and into the vertebral bodies.

These components provide the necessary stability both in tension and compression to achieve immobilization.

It has been found that when a pair of spinal rods are fastened in parallel on either side of the spinous process, the assembly can be significantly strengthened by using at least one additional rod to horizontally bridge the pair of spinal rods. An example of a cross brace assembly of this type is disclosed in U.S. Pat. No. 5,084,049. Devices such as these commonly consist of a threaded rod for providing the desired lateral support. The threaded rod is fastened to each of the spinal rods by clamps located on each end thereof. However, this configuration is bulky and can cause irritation of the patient's back muscles and other tissue which might rub against the device. A cross brace assembly that overcomes the problems associated with bulky stabilization assemblies by fitting closer to the spine, preferably in the same general plane as the cylindrical spinal rods, is disclosed in commonly assigned U.S. Pat. No. 5,989,251.

It has also been found that the distance between a pair of spinal rods located on either side of the spine can vary depending upon the anatomy of the patient and the manner in which the rods are secured to the spinous process. Thus, transverse rod connectors have been designed with adjustable bridging structures to accommodate this variability, as disclosed, for example, in U.S. Pat. Nos. 5,752,955 and 5,947,966.

Most existing transverse connectors consist of rods, plates, and bars linked to the longitudinal rods by coupling mechanisms with set screws, nuts, or a combination of each.

These connectors require several components and instruments to build the constructs. Each additional component or instrument required to assemble the connectors adds to the complexity of the surgical procedure. Examples of connectors constructed from multiple components are disclosed in U.S. Pat. Nos. 5,312,405, 5,334,203 and 5,498,263.

It would be beneficial to provide an improved device to transversely connect spinal rods of a spinal stabilization system to one another which utilizes a minimum number of components parts and surgical instrumentation, and which has a low-profile so as to fit closely to the spine, and which may be easily adjusted during a spinal stabilization procedure.

SUMMARY OF THE DISCLOSURE

The subject disclosure is directed to an apparatus for connecting two conventional spinal rods of a spinal stabilization system to one another in such a manner so as to provide an adjustable low-profile rigid linkage therebetween. In accordance with a preferred embodiment of the subject disclosure, the apparatus includes an elongated body portion and a clamp portion depending from the body portion for engaging a spinal rod.

Preferably, the clamp portion defines a deflectable clamp body having opposed clamp arms configured for movement between a first position wherein a spinal rod is received between the opposed clamp arms of the clamp body and a second position wherein the spinal rod is securely engaged by the opposed clamp arms of the clamp body. In addition, structural means are operatively associated with the clamp body to effectuate the movement of the opposed clamp arms of the clamp body between the first and second positions.

In accordance with one aspect of the disclosure, the structural means for moving the opposed clamp arms between the first and second positions comprises a cam lug configured for reception within a bore formed in the clamp body and adapted for axial rotation within the bore. The cam lug has a generally cylindrical body with camming surfaces formed thereon, and the reception bore is defined at least in part by interior walls. In operation, the camming surfaces of the cam lug are adapted and configured for bearing against the interior walls of the reception bore upon rotation of the cam lug within the reception bore.

In accordance with another aspect of the subject disclosure, the structural means for moving the opposed clamp arms between the first and second positions comprises an engagement tab projecting outwardly from an exterior surface of the clamp body, and a recess formed within the clamp body spaced from the engagement tab. In operation, the engagement tab is grasped with a tool and pulled outwardly to enlarge a gap between the opposed clamp arms.

In accordance with one aspect of the subject disclosure the elongated body portion has a predetermined span length for extending between a pair of elongated spinal rods disposed in parallel relationship. Alternatively, the elongated body portion has a span length that is selectively variable for extending between a pair of elongated spinal rods disposed in parallel relationship. Accordingly, the elongated body portion includes means for selectively adjusting the length of the body portion.

In accordance with one aspect of the subject disclosure, the means for selectively adjusting the length of the body portion includes a first body portion having an axial bore defined therein and a second body portion having an axial shaft for reception within the axial bore of the first body portion, and a locking ring for radially compressing the first body portion against the second body portion when the axial shaft is disposed within the axial bore. In accordance with another aspect of the subject disclosure, the means for selectively adjusting the length of the body portion includes a first body portion having a threaded bore defined therein and a second body portion having an threaded shaft for reception within the threaded bore of the first body portion.

These and other unique features of the apparatus disclosed herein and the method of installing the same will become more readily apparent from the following description of the drawings.

BRIEF DESCRIPTION OF THE DRAWINGS

So that those having ordinary skill in the art to which the disclosed apparatus appertains will more readily understand how to construct and use the same, reference may be had to the drawings wherein:

FIG. 1 is a perspective view of a spinal stabilization system for immobilizing a region of the spinal column which includes variable and fixed length rod connecting apparatus constructed in accordance with preferred embodiments of the subject disclosure, and a set of bone screws with linear locking mechanisms;

FIG. 1A a perspective view of another spinal stabilization system for immobilizing a region of the spinal column which includes a set of bone screws with top-loading rotatable locking mechanisms;

FIG. 2 is a top plan view of the spinal stabilization system of FIG. 1 implanted on the posterior side of the spinal column;

FIG. 3 is a perspective view of the variable length rod connecting apparatus of the subject disclosure with the parts thereof separated for ease of illustration;

FIG. 4 is a perspective view of the fixed length rod connecting apparatus of the subject disclosure;

FIG. 5 is a cross-sectional view taken along line 5-5 of FIG. 1 illustrating the clamping portion of the rod connecting apparatus of FIG. 3 in fastened condition;

FIG. 6 is a perspective view of the cam lug of the subject disclosure which facilitates movement of the clamping portion of the rod connecting apparatus of FIGS. 3 and 4 between first and second positions;

FIG. 7 is a top plan view of the cam lug illustrated in FIG. 6 showing the opposed lateral cam surfaces thereof;

FIG. 8 is a perspective view of the variable length rod connecting apparatus of FIG. 3 prior to installation between a pair of parallel I spinal rod;

FIG. 9 is a perspective view of the variable length rod connective apparatus shown in FIG. 8, with the clamping portions thereof engaged to the spinal rods in a frictionally engaged condition;

FIG. 10 corresponds to the operative step shown in FIG. 9 and illustrates the relative movement of the arms of the clamping portion between an initial position and a frictionally engaged position with respect to a spinal rod extending therethrough prior to being moved into a tightly secured position about the periphery of the spinal rod;

FIG. 11 is a perspective view of the variable length rod connecting apparatus shown in FIGS. 7 and 8, with the locking collet moved into a locked position to maintain the length of the connector using a surgical instrument;

FIG. 12 is a perspective view of the variable length rod connecting apparatus shown in FIGS. 7 and 8, illustrating the positioning of the cam lugs into the reception areas of the clamping portions;

FIG. 13 is a perspective view of the variable length rod connecting apparatus shown in FIG. 12, illustrating the rotation of the cam lugs to facilitate movement of the clamping portions into a securely fastened position to fixedly connect the apparatus to the spinal rods;

FIG. 14 is a perspective view of another variable length rod connecting apparatus constructed in accordance with a preferred embodiment of the subject disclosure with the parts thereof separated for ease of illustration;

FIG. 15 is a perspective view of still another variable length rod connecting apparatus constructed in accordance with a preferred embodiment of the subject disclosure with the parts thereof separated for ease of illustration; and FIG. 16 is a perspective view of a kit containing various components and tools constructed in accordance with the subject disclosure.

These and other features of the apparatus disclosed herein will become more readily apparent to those having ordinary skill in the art from the following detailed description of the invention taken in conjunction with the drawings.

DETAILED DESCRIPTION OF THE PREFERRED EMBODIMENTS

Referring now to the drawings wherein like reference numerals identify similar structural elements of the subject apparatus, there is illustrated in FIGS. 1 and 2 a spinal stabilization system constructed in accordance with a preferred embodiment of the subject disclosure and designated generally by reference numeral 10.

Referring to FIG. 1, spinal stabilization system 10 includes a pair of elongated spinal rods 12 and 14. The spinal rods are adapted for parallel deployment on either side of the spinous process, as illustrated in FIG. 2. Spinal rods 12 and 14 are of a conventional type, constructed from a bio-compatible material and having a circular cross-section with a smooth outer surface finish. Spinal rods 12 and 14 are segmentally secured to the bones of the spinous process by a variety of structural components including, for example, bone screws 18.

Bone screws 18 have linear locking mechanisms of the type disclosed in commonly assigned U.S. Pat. No. 5,989,251, the disclosure of which is herein incorporated by reference in its entirety. An alternative spinal stabilization system designated generally by reference numeral 10a is illustrated in FIG. 1A. Spinal stabilization system 10a includes bone screws 18a that have top-loading rotatable locking mechanisms of the type disclosed in commonly assigned U.S. application Ser. No. 09/487,942, the entirety.

It has been found that when a pair of spinal rods are fastened to one another in parallel relationship on either side of the spinous process, as illustrated in FIGS. 1 and 2, the stabilization system can be significantly strengthened. Thus, the spinal rods 12 and 14 of stabilization system 10 are connected to one another by a plurality of rod linking devices constructed in accordance with a preferred embodiment of the subject disclosure. FIGS. 1 and 2 illustrate two embodiments of the rod linking device of the subject disclosure constructed from high-strength, low-weight, corrosion resistant, biocompatible metal alloy, such as, for example, titanium or stainless steel.

The first embodiment is a variable length rod linking device designated generally by reference numeral 20. (See FIG. 3). The second embodiment has a fixed length and is designated by reference numeral 60. (See FIG. 4). Rod linking device 20 is adapted and configured to be selectively adjusted during a spinal stabilization procedure to bridge the gap that exists between spinal rod 12 and 14. In contrast, rod linking device 60 has a predetermined span length and is configured to bridge a fixed gap between spinal rods 12 and 14. As discussed in greater detail hereinbelow, rod linking devices 20 and 60, also referred to herein as transverse rod connectors 20 and 60, both have a unique rod engaging system in the form of a generally u-shaped deflectable clamping portion or hook.

Referring now to FIG. 3, there is illustrated the variable length rod linking device 20 of the subject disclosure. Rod connector 20 includes first and second body portions 22 and 24. The distal section 22d of the first body portion 22 has a slight outward taper so that the outer diameter of the distal section 22d is slightly greater than that of the main section of the first body portion 22. In addition, an axial reception bore 26 is defined in the first body portion 22 for receiving the second body portion 24. An annular locking collet 28 is operatively associated with the first body portion 22 for securely retaining the second body portion 24 within the axial reception bore 26. More particularly, the distal section 22d of the first body portion 22 has a pair of diametrically opposed compression slots 30a and 30b defined therein, which extend from the free distal end of body portion 22 to a location intermediate its length, to facilitate radial compression of the distal end section 22d of body portion 22 against the second body portion 24 when it is disposed within axial bore 26.

Annular locking collet 28 is coaxially positioned on body portion 22 and is configured for axial movement along the length thereof, between an annular blocking flange 34 disposed intermediate the length of body potion 22 and a pair of diametrically opposed blocking ribs 36a and 36b disposed at the free distal end of body portion 22. In use, movement of the locking collet 28 between an initial position adjacent annular blocking flange 34 and a final position adjacent blocking ribs 36a and 36b causes radial compression of the distal end section 22d of body portion 22, as the locking collet 28 moves relative to the outwardly tapered distal section 22d of body portion 22.

As best seen in FIG. 3, blocking ribs 36a and 36b are dimensioned and configured to facilitate the mounting of locking collet 28 on body portion 22 during assembly of the connector 20. More specifically, during assembly, locking collet 28 is slid over blocking ribs 36a and 36b for positioning within the area defined between the blocking ribs and annular blocking flange 34. Manipulation of locking collet 28 is aided by the provision of tab 28a. Also shown in FIG. 3 is a location guide hole 38 disposed between the free distal end of body portion 22 and the annular blocking flange 34. The hole 38 enables a surgeon to locate the position of the collet 28 during locking to ensure collet 28 is moved sufficiently axially to the final locking position.

The second body portion 24 of rod connector 20 is defined by an axial shaft having a uniform outer diameter along substantially the entire length thereof. The outer diameter of the axial shaft is about approximately equal to the inner diameter of the axial bore 26 defined within the first body portion 22, so that an interference fit exists therebetween when the two components are telescopically connected to one another during assembly. A retaining ring 24a is provided to retain first and second body portions 24 and 22 together, when assembled, as a lip (not shown) on first body portion 22 engages the larger diameter retaining ring 24a.

With continuing reference to FIG. 3 in conjunction with FIGS. 5 through 7, rod connector 20 includes a unique rod engaging system for securely fastening the transverse connector to spinal rods 12 and 14 during a spinal stabilization procedure with imparting undue stress upon the spine. This system consists of deflectable rod clamps 42 and 44 which depends from the first and second body portion 22 and 24, respectively, for securely engaging spinal rods 12 and 14, respectively. Rod clamp 42 depending from body portion 22 includes a first and second clamp arms 42a and 42b between which is defined a gap or channel 43a for accommodating spinal rod 12. Similarly, rod clamp 44 which depends from body portion 24 includes first and second opposed clamp arms 44a and 44b between which is defined a gap or channel 43b. Each rod clamp 42, 44 has a respective reception port 46, 48 for receiving a camming lug 50. The camming lug 50 is configured to effectuate movement of a clamp 42, 44 from an initial position wherein the clamp Is frictionally engaged with a spinal rod to a final position wherein the clamp is tightly compressed about the periphery of the spinal rod, as shown in FIG. 5.

Referring to FIGS. 6 and 7, camming lug 50 includes a main body portion 52, illustratively generally elliptical in cross section, with enlarged radially outwardly projecting curved lateral camming surfaces 52a and 52b for interacting with the interior walls of reception ports 46, 48. Camming lug 50 further includes a central aperture 54 for receiving an appropriate tool or implement designed to facilitate axial rotation of camming lug 50 within reception ports 46, 48 during a spinal stabilization procedure (see FIG. 13). Advantageously, the rotational forces imparted upon camming lug 50 during assembly do not impose undue stress on the patient's spine during a stabilization procedure. A retention flange 56 is provided at the lower end of the main body portion 52 of camming lug 50 for cooperating with retention channels 46a, 48a formed in reception portions 46, 48, respectively. This interaction is intended to inhibit the displacement of the camming lugs from the reception ports during shipment, as well as during a surgical procedure.

In use, rotation of the camming lug 50 within reception ports 46, 48 causes the lateral camming surfaces 52a, 52b to bear against the walls of reception ports 46, 48, urging the walls to expand radially outwardly. In what can best be described as a scissors-like action, the outward expansion of the port walls causes the clamp arms 42a, 42b and 44a, 44b to move inwardly toward one another so as to reduce the size or diameter of the gaps or channels 43a, 43b defined therebetween, respectively. As a result, spinal rods 12 and 14 are compressed tightly between clamp arms 42a, 42b and 44a, 44b, as illustrated, for example, in FIG. 5. It should be recognized that the amount of outward deflection of the walls of the reception bore caused by rotating the canning lugs, and the resultant inward compression of the clamp arms is relatively small, as the arms must only move a sufficient distance so as to clamp about the spinal rod after having already achieved a frictional engagement therewith upon initial assembly.

Referring now to FIGS. 8 through 13, there is illustrated, in sequential order, one embodiment of the operative steps associated with mounting the rod linking device 20 of the subject disclosure to a pair of parallel spinal rods 12 and 14 during a spinal stabilization procedure. As illustrated in FIG. 8, initially the rod linking device 20 is moved into approximation with spinal rods 12 and 14 with the body portions 22 and 24 telescopically mated to one another, i.e., body portion 24 is disposed within the axial reception bore 26 of body portion 22. At such a time, locking collet 28 is positioned intermediate the distal end section 22 of body portion 22, proximal of compression slots 30a and 30b, and the outwardly tapered portion of the distal section 22d.

Then, as illustrated in FIG. 9, the rod clamps 42, are brought into engagement with spinal rods 12 and 14, respectively. At such a time, the rod clamps are not securely fastened to the spinal rods and may moved along the length of the spinal rods or be removed from the rods by the surgeon for repositioning if such action becomes necessary. FIG. 10 illustrates the engagement of a rod clamp with a spinal rod, whereby the "broken lines" illustrate the clamp in a non-engaged position and the "solid lines" illustrate the rod clamp in a frictionally engaged position.

Referring to FIG. 11, after rod clamps 42 and 44 are engaged to spinal rod 12 and 14, respectively, the length of rod linking device 20 is set. This is accomplished by moving locking collet 28 from its initial location adjacent blocking flange 34 toward the blocking ribs 36a and 36b. This movement is accomplished by an appropriate tool, such as surgical pliers 70 or a similar surgical instrument. As the collect 28 translates in the direction of arrow "A", it moves against the tapered surfaces of the distal end section 22d of body portion 22, causing the distal end section 22d of body portion 22 to radially compress against the cylindrical outer surface of body portion 24 disposed within axial bore 26. When locking collet 28 is moved past location guide hole 38, the user is informed that it is in the locked position.

Referring to FIG. 12, once the appropriate span length of rod linking device 20 has been set, camming lugs 50 are inserted into the reception ports 46 and 48 of deflectable rod clamp 42 and 44. At such a time, the camming surfaces 50a and 50b of the camming lugs are not bearing against the walls of the reception ports within which they are disposed. Consequently, the position of the rod clamps can still be adjusted if such action is necessary. It is contemplated in a preferred embodiment that the system is shipped and utilized with the camming lugs 50 already in reception ports 46 and 48. Thus, in this embodiment, in the steps shown in FIGS. 8, 9 and 11 the camming lugs would already be in place, saving the surgeon the additional step of inserting the individual camming lugs 50 in reception ports 46, 48.

Alternatively, it is envisioned that the rod linking devices of the subject disclosure could be shipped with the camming lugs 50 already positioned within the reception ports 46, 48 so as to reduce the number of steps required to secure the spinal rods 12, 14 to one another during a spinal stabilization procedure. Thus, the operative step illustrated in FIG. 12 would become unnecessary.

In either instance, to securely fasten the rod clamps 42, 44 to spinal rods 12, 14, camming lugs 50 are axially rotated in a clock-wise direction within reception ports 46, 48 using an appropriate surgical tool or implement, such as for example, lug driver 75. This axial rotation causes the outwardly projecting camming surfaces 52a, 52b to bear against the interior walls of the reception ports 46, 48, urging them to move radially outwardly. As a result, an equal and opposite scissors-like movement of the opposed clamp arms occurs, causing the opposed clamp arms of each rod clamp 42,44 to tightly engage the outer periphery of the spinal rods 12, 14, as best seen, for example, in FIG. 5, without imparting undue stress on the spine. Once tightly engaged about the spinal rods, the rod clamps 42, 44 are essentially immobilized.

While the operative steps involved in mounting and securing rod linking device 20 to a pair of spinal rods has been described with respect to a sequential order, it will be readily apparent to those having ordinary skill in the art to which the subject disclosure appertains that the order or sequence of the operative steps can be altered or modified. For example, in an alternative and preferred embodiment, the rod clamps can be secured to the spinal rods prior to setting the desired length of the linking device. In this preferred version, the camming lugs 50 are rotated to the clamps 42 and 44 on the spinal rods and then the locking collet 28 is moved axially to its final locking position.

Referring to FIG. 4, the rod linking device 60 of the subject disclosure has a predetermined span length configured to extend a fixed distance across the spinous process between a pair of parallel spinal rods 12 and 14, as illustrated in FIGS. 1 and 2. Rod linking device 60 includes a main body portion 62 defining a longitudinal axis. Body portion 62 has a low profile construction for fining closely to the spine, so as to reduce any bulkiness associated with spinal stabilization system 10. Deflectable rod clamps 72 and 74 depend from the opposed ends of the main body portion 62 for securely engaging spinal rods 12 and 14, respectively. Rod clamps 72, 74 are substantially identical to rod clamps 42,44 of rod connector 20 and include reception ports 76, 78, respectively for receiving camming lugs 50. As in the previous embodiment, camming lugs 50 are configured to effectuate movement of the opposed clamp arms of rod clamps 72, 74 from an initial position in frictional engagement with the spinal rods to a final position tightly secured about the periphery of the spinal rods.

Rod linking device 60 is preferably provided in several different span lengths ranging from about 16 mm in length to about 24 mm in length, in about 2 mm increments. Additional lengths with varying increments are also contemplated. Referring to FIG. 16, in accordance with the subject disclosure a kit 100 is provided defined by a packing enclosure 110 containing, among other things, a plurality of rod linking devices 60a-60c, each of which has a different preset span length for bridging the gap between a pair of elongated spinal rods. For example, the kit 100 could include a rod connector 60a having a span length of about 16 mm, a rod connector 60b having a span length of about 18 mm, and, rod connector 60c having a span length of about 20 mm.

Preferably, the rod connectors 60a-60c would be packaged with camming lugs 50 already installed in the reception ports of the of clamps of each connector. Alternatively, a plurality of camming lugs 50 could be provided in the package separate from the connectors. The kit would also include an lug driver 75 for securing the camming lugs 50 within the reception ports of the linking devices. It is envisioned that kit 100 could also contain a plurality of variable length rod linking devices 20a-20c and an appropriate surgical instrument 70 for moving the locking collet 28 along the length of the body portion, as described hereinabove with respect to FIG. 11.

Referring to FIG. 14, there is illustrated another rod linking device constructed in accordance with a preferred embodiment of the subject disclosure designated generally by reference number 80. Rod linking device 80 is a variable length connector that includes first and second telescopically associated body portions 82 and 84 that are substantially similar to the first and second body portion 22 and 24 of rod linking device 20, which is described hereinabove and illustrated in FIG. 3. The first and second body portions 82, 84 of rod linking device 80 differ from those of rod linking device 20 in that the rod clamps 92, 94 thereof do not employ camming lugs 50 to effectuate movement of the opposed clamp arms 92a, 92b and 94a, 94b into a tightly engaged position about the periphery of the spinal rods. Instead, the gaps 93a, 93b defined between the opposed arms of each rod clamp 92, 94 are dimensioned and configured to tightly engage the periphery of the spinal rods without using a camming lug.

To engage a rod clamp 92, 94 to a spinal rod, the gap 93a, 93b between the opposed clamp arms thereof of is radially expanded to allow the rod to enter the gap. This is accomplished by gripping a tab 96, 98 projecting outwardly from the leading edge of each rod clamp 92, 94 with an appropriate surgical instrument or tool (not shown), and drawing the outer clamp arm 92a, 94a away from the inner clamp arm 92b, 94b. The deflection of the rod clamp 92, 94 and resultant radial expansion of the gap 93a, 93b is aided by the provision of cross-slots 95, 97 formed in rod clamps 92, 94 which provide areas within which the upper portion of the outer clamp arms 92a, 94a can effectively translate during the radial expansion of the gaps 93a, 93b. Once a spinal rod is situated within the gap 93a, 93b, the tab 96, 98 is released by the surgeon, allowing the outer clamp arm 92a, 94a to return to its normal position. Thereupon, the inner diameter of the gap 93a, 93b is substantially equal to the outer diameter of the spinal rod and the rod connector 80 is essentially immobilized.

Referring to FIG. 15, there is illustrated yet another rod linking device constructed in accordance with a preferred embodiment of the subject disclosure designated generally by reference number 120. Rod linking device 120 is also a variable length rod connector in that the span length thereof may be selectively and easily adjusted by a surgeon during a spinal stabilization procedure to accommodate different anatomical conditions. Rod linking device 120 includes a first body portion 122 which has an internally threaded axial bore 126 extending therethrough for receiving a corresponding threaded shaft which defines the second body portion 124. During assembly, the second body portion 124 is threadably secured within the internal bore 126 of the first body portion 122 to set the desired span length of rod linking device 120.

The body portions 122 and 124 of rod linking device 120 include deflectable rod clamps 142 and 144, respectively for securing engaging spinal rods rod during a surgical procedure. In contrast to the rod clamps of rod connectors 20, 60 and 80, described hereinabove, rod clamps 142, 144 do not include additional structures to facilitate movement of the opposed clamp arms 142a, 142b and 144a, 144b into a securely engaged position. Instead, the opposed clamp arms of rod clamps 142, 144 are simply snap-fit onto the spinal rods during a surgical procedure, so that the opposed clamp arms of the rod clamps are tightly engaged about the periphery of the spinal rods.

Although the apparatus disclosed herein has been described with respect to preferred embodiments, it is apparent that modifications and changes can be made thereto without departing from the spirit and scope of the invention as defined by the claims. For example, while each embodiment of the subject rod linking device has been described in conjunction with a particular type of deflectable rod clamping mechanism, it is envisioned and well within the scope of the subject disclosure that the various rod clamping mechanisms disclosed herein are easily interchangeable with respect to one another.

The invention claimed is:

1. A method of connecting spinal rods comprising:
providing a rod connector having an elongated body with a first end and a second end, one of said first or second ends having a first deflectable rod clamp formed integral with the elongated body, said first clamp having opposed first clamp arms capable of moving between a first position and a second position and a first cam lug adapted for axial rotation within a first bore formed in said first clamp;
inserting a first spinal rod between the first clamp arms when the first clamp arms are in the first position; and
rotating the first cam lug within the first bore to impart a force on interior walls of the first bore thereby moving the first clamp arms of said first clamp to the second position to securely engage the first spinal rod therebetween.

2. The method according to claim 1, further comprising the steps of implanting a plurality of pedicle screws in a plurality of vertebrae and connecting the first spinal rod to the pedicle screws.

3. The method according to claim 1, wherein the elongated body has a predetermined span length for extending between a pair of elongated spinal rods.

4. The method according to claim 1, further comprising the step of selectively adjusting the length of the elongated body by positioning a first body portion of the elongated body with respect to a second body portion of the elongated body.

5. The method according to claim 4, wherein the adjusting step includes telescopically positioning the first body portion with respect to the second body portion and locking the first body portion with respect to the second body portion.

6. The method according to claim 5, wherein the locking step includes positioning a locking ring to radially compress the first body portion against the second body portion.

7. The method according to claim 4, wherein the adjusting step includes threading a threaded shaft of the second body portion within a threaded bore of the first body portion.

8. The method according to claim 1, wherein the other of said first or second ends of the elongated body includes a second deflectable rod clamp formed integral with the elongated body, said second clamp having opposed second clamp arms capable of moving between a first position and a second position and a second cam lug adapted for axial rotation within a second bore formed in said second clamp.

9. The method according to claim 8, further comprising the step of inserting a second spinal rod between the second clamp arms when the second clamp arms are in the first position.

10. The method according to claim 9, further comprising the step of rotating the second cam lug to impart a force on both second clamp arms thereby moving the second clamp arms of said second clamp to the second position to securely engage the first spinal rod therebetween.

11. The method according to claim 10, further comprising the steps of implanting a plurality of pedicle screws in a plurality of vertebrae and connecting the second spinal rod to the pedicle screws.

12. The method according to claim 10, wherein the elongated body has a predetermined span length for extending between a pair of elongated spinal rods.

13. The method according to claim 10, further comprising the step of selectively adjusting the length of the elongated body by positioning a first body portion of the elongated body with respect to a second body portion of the elongated body.

14. A method of connecting spinal rods comprising:
providing a rod connector having a first body member including a first clamp formed integral therewith, the first clamp having arms capable of moving between a rod receiving position and a rod clamping position, and a second body member including a second clamp formed integral therewith, the second clamp having arms capable of moving between a rod receiving position and a rod clamping position;
engaging a first spinal rod with the first clamp and engaging a second spinal rod with the second clamp;
positioning the first body member with respect to the second body member based on the position of the first and second spinal rods with respect to each other;

locking a locking collet operatively associated with the first and second body members to prevent movement of the first body member with respect to the second body member; and securing the first and second clamps to the first and second spinal rods, respectively, the securing step including rotating a first cam lug adapted for axial rotation within a first bore formed in the first clamp, and rotating a second cam lug adapted for axial rotation within a second bore formed in the second clamp, the rotating of the first and second cam lugs imparting a force on interior walls of the first and second bores thereby causing the first and second clamp arms to move to the rod clamping position.

15. The method according to claim 14, wherein the first body member further includes a first end portion defining the first clamp for engaging the first spinal rod and a second end portion defining an axial bore with a radially compressible opening, the second body member including a third end portion defining the second clamp for engaging the second spinal rod and a fourth end portion defining an axial shaft dimensioned and configured for reception within the axial bore of the first body member.

16. The method according to claim 15, wherein the locking step includes sliding the locking collet between a first position wherein the annular collet is spaced from the radially compressible opening of the axial bore of the first body member, and a second position wherein the annular collet surrounds and compresses the radially compressible opening of the axial bore.

17. The method according to claim 14, wherein said engaging step further includes gripping tabs projecting from exterior surfaces of the clamps to deflect the clamp arms to the rod receiving position.

18. A method of immobilizing the spine comprising:
implanting at least two bone screws in each of a plurality of vertebrae, each vertebrae having at least one screw on a first side and at least one screw on a second side;

affixing a first spinal rod to the bone screws on the first side and a second spinal rod to the bone screws on the second side;

connecting the first and second spinal rods with a rod connector having an elongated body portion with opposed ends and rod clamps formed integral with the elongated body portion and depending from each end, each rod clamp defining a deflectable clamp body having opposed clamp arms capable of moving between a first position for receiving the spinal rods and a second position for securely engaging the spinal rods; and allowing the rod connector to remain engaged with the first and second spinal rods, wherein said connecting step further includes rotating cam lugs adapted for axial rotation within bores formed in the clamp bodies, the rotating of each cam lug imparting a force on interior walls of each bore, respectively, thereby causing the clamp arms to move to the second position.

19. The method according to claim 18, further comprising the step of selectively adjusting the length of the elongated body by positioning a first body portion with respect to a second body portion.

20. The method according to claim 19, wherein the adjusting step includes telescopically positioning the first body portion with respect to the second body portion and locking the first body portion with respect to the second body portion.

21. The method according to claim 20, wherein the locking step includes positioning a locking ring to radially compress the first body portion against the second body portion.

* * * * *

UNITED STATES PATENT AND TRADEMARK OFFICE
CERTIFICATE OF CORRECTION

PATENT NO. : 8,025,679 B2  
APPLICATION NO. : 11/062510  
DATED : September 27, 2011  
INVENTOR(S) : David Nichols and Eric Finley Page 1 of 1

It is certified that error appears in the above-identified patent and that said Letters Patent is hereby corrected as shown below:

Title page  
Column 2, line 9 of Abstract, "&ms" should read -- arms --.  
Column 2, line 10 of Abstract, "&the" should read -- and --.  
Column 2, line 11 of Abstract, "which h" should read -- which is --.

Signed and Sealed this  
First Day of September, 2015

Michelle K. Lee  
*Director of the United States Patent and Trademark Office*